US010789737B2

(12) United States Patent
Wang et al.

(10) Patent No.: US 10,789,737 B2
(45) Date of Patent: Sep. 29, 2020

(54) TOMOGRAPHIC IMAGE ACQUISITION USING ASYMMETRICAL PIXEL BINNING

(71) Applicant: CARESTREAM HEALTH, INC., Rochester, NY (US)

(72) Inventors: Xiaohui Wang, Pittsford, NY (US); Richard A. Simon, Rochester, NY (US); Levon O. Vogelsang, Webster, NY (US); Nathan J. Packard, Provo, UT (US)

(73) Assignee: Carestream Health, Inc., Rochester, NY (US)

( * ) Notice: Subject to any disclaimer, the term of this patent is extended or adjusted under 35 U.S.C. 154(b) by 61 days.

(21) Appl. No.: 15/780,400

(22) PCT Filed: Dec. 20, 2016

(86) PCT No.: PCT/US2016/067662
§ 371 (c)(1),
(2) Date: May 31, 2018

(87) PCT Pub. No.: WO2017/112623
PCT Pub. Date: Jun. 29, 2017

(65) Prior Publication Data
US 2018/0350112 A1    Dec. 6, 2018

Related U.S. Application Data

(60) Provisional application No. 62/270,610, filed on Dec. 22, 2015.

(51) Int. Cl.
G06T 11/00 (2006.01)
A61B 6/02 (2006.01)
(Continued)

(52) U.S. Cl.
CPC ............ *G06T 11/005* (2013.01); *A61B 6/025* (2013.01); *A61B 6/032* (2013.01); *A61B 6/4007* (2013.01);
(Continued)

(58) Field of Classification Search
CPC ........ A61B 6/032; A61B 6/025; A61B 6/5205; A61B 6/4007; A61B 6/4208;
(Continued)

(56) References Cited

U.S. PATENT DOCUMENTS 7,583,786 B2    9/2009  Jing et al.
2008/0031407 A1*  2/2008  Satta .................... A61B 6/032
                                                      378/15

(Continued)

OTHER PUBLICATIONS

International Search Report for International Application No. PCT/US2016/067662 dated Mar. 10, 2017, 2 pages.

*Primary Examiner* — Daniel G Mariam

(57) ABSTRACT

A computer implemented method for reconstructing a 3-D volume image using a radiographic imaging system having one or more x-ray sources and a digital detector. A plurality of radiographic images of a subject at various angles are captured in the digital detector. Image data in two or more pixels of the detector that are adjacent to each other in a row direction or a column direction are combined, while pixels adjacent in the other direction are not combined.

18 Claims, 13 Drawing Sheets

(51) Int. Cl.
*A61B 6/03* (2006.01)
*H04N 5/347* (2011.01)
*A61B 6/00* (2006.01)
*A61B 8/08* (2006.01)
*H04N 5/32* (2006.01)

(52) U.S. Cl.
CPC .......... *A61B 6/4085* (2013.01); *A61B 6/4208* (2013.01); *A61B 6/4233* (2013.01); *A61B 6/466* (2013.01); *A61B 6/5205* (2013.01); *A61B 8/5207* (2013.01); *G06T 11/006* (2013.01); *H04N 5/32* (2013.01); *H04N 5/347* (2013.01); *G06T 2210/41* (2013.01)

(58) Field of Classification Search
CPC ..... A61B 6/4085; A61B 6/4233; A61B 6/466; A61B 6/5207; G06T 11/005; G06T 11/006; G06T 2210/41
USPC ........................................................ 382/154
See application file for complete search history.

(56) References Cited

U.S. PATENT DOCUMENTS

| | | | |
|---|---|---|---|
| 2009/0041191 A1* | 2/2009 | Suzuki | A61B 6/14 378/98.5 |
| 2013/0083886 A1 | 4/2013 | Carmi et al. | |
| 2015/0230765 A1* | 8/2015 | Ma | A61B 6/4042 378/62 |
| 2015/0324973 A1 | 11/2015 | Ueki et al. | |
| 2016/0061966 A1* | 3/2016 | Kim | A61B 6/4233 250/370.09 |
| 2016/0106382 A1* | 4/2016 | Lu | A61B 6/482 600/428 |

* cited by examiner

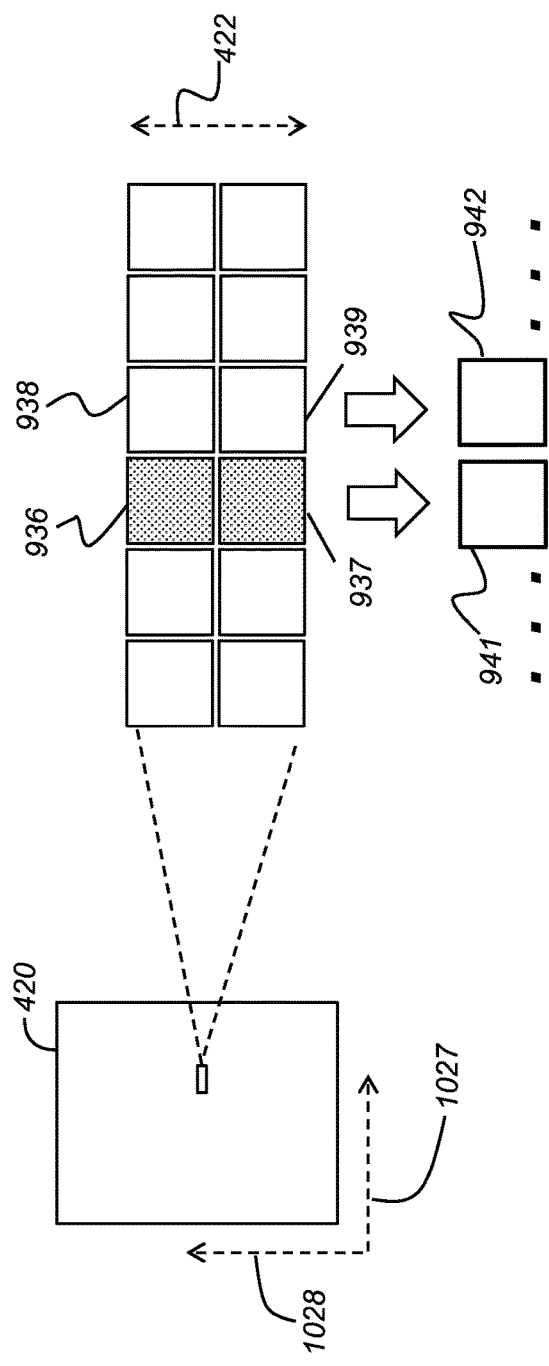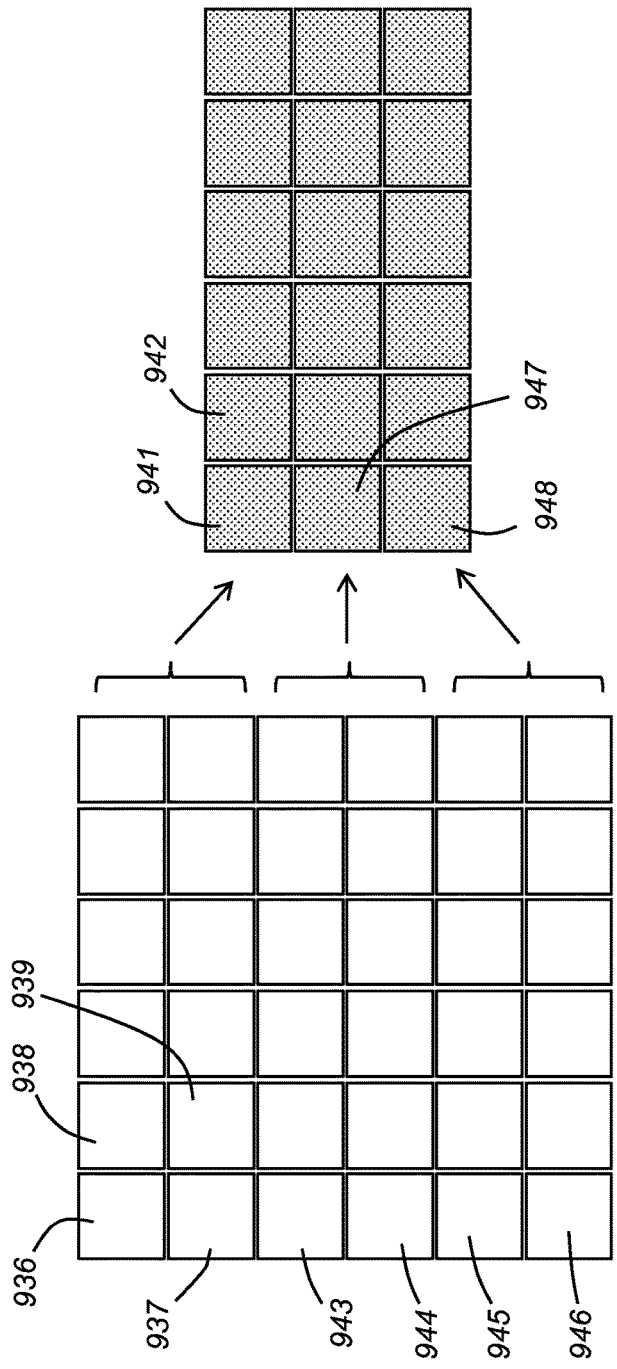

TOMOGRAPHIC IMAGE ACQUISITION USING ASYMMETRICAL PIXEL BINNING

CROSS REFERENCE TO RELATED APPLICATIONS

This application claims the benefit of and is a U.S. National Phase filing of PCT Application PCT/US2016/067662 filed Dec. 20, 2016 entitled "TOMOGRAPHIC IMAGE ACQUISITION USING ASYMMETRICAL PIXEL BINNING, in the name of Wang et al., which claims benefit of U.S. Provisional application Ser. No. 62/270,610, provisionally filed on Dec. 22, 2015, entitled "TOMOGRAPHIC IMAGE ACQUISITION USING ASYMMETRICAL PIXEL BINNING', in the name of Wang et al, all of which are incorporated herein in their entirety.

BACKGROUND OF THE INVENTION

The disclosure relates generally to the field of tomographic imaging and more particularly to apparatus and methods for processing image data acquired from a radiographic imaging system using a digital detector to capture images used for computed tomography and tomosynthesis imaging.

In computed tomography (CT) the x-ray source and the detector revolve about a subject under examination to capture a set of radiographic projection images (2-D) at different revolution angles. A computer is then used to mathematically reconstruct, from the set of projection images, a 3-D image volume representing the internal structure of the subject. In order to obtain accurate density data for the volume, the angular coverage for the full CT exam is usually greater than 180 degrees, preferably 360 degrees.

Tomosynthesis works similarly to CT by acquiring images at different angular positions but over a smaller angular range than CT, and tomosynthesis may not require moving both the detector and x-ray source about the subject. Consequently, tomosynthesis techniques typically capture less depth information about the subject. The scan path of the x-ray source and/or the detector for tomosynthesis may be linear, arcuate, curved, or may have a circular arrangement. The set of images that is acquired using tomosynthesis imaging, although incomplete with regard to full volume image information obtained using computed tomography, is digitally processed to yield a 3-D image similar to computed tomography but with a more limited spatial resolution in the depth direction. Depth data is reconstructed from the captured projection images in the form of a number of slices through the patient anatomy, with the best spatial resolution obtained in the slices parallel to the plane of the detector (in-plane resolution). A consequence of limited angular scanning for tomosynthesis imaging is that the depth resolution is characteristically lower than a standard CT, but the in-plane resolution may be much higher due to the use of high resolution x-ray detectors in tomosynthesis.

The various types of tomographic imaging techniques obtain image depth information by changing the relative angle between the x-ray source and the subject for each projection image. This change is generally accomplished by movement of the x-ray source relative to a patient, with or without corresponding movement of the detector. In applications where the detector is fixed, one or more movable x-ray sources may be displaced in a motion direction to vary the angle at which radiation from the source is directed through the subject toward the detector. Where an array of x-ray sources is used, the relative angle may be effectively changed by energizing successive elements of the array synchronously with image capture in the detector. Since the 3-D volume image is digitally generated and represented, various processing techniques may be used to generate and present a series of 2-D slices at different depths of the volume and with different thicknesses, all reconstructed from the same 3-D generated image.

Patient motion during any tomographic exam is a concern due to increased risk of blurring the anatomical details in the reconstructed 3-D image. Reducing scan time is one of the most effective solutions to mitigate patient motion artifacts in the reconstructed images. However, in both CT and tomosynthesis imaging, a significant limiting factor for reducing the scan time is the detector's rate of reading out image data frames. During a detector readout procedure, a large amount of raw projection image data is acquired, converted to digital data, and processed in order to obtain sufficient projection image data for reconstruction. As an example of the readout time's impact on scan time—for a typical tomosynthesis chest exam using 60 projection images captured at 5 frames per second, the total scan time is 12 seconds. For patients who are in poor condition, it may be challenging to suspend breathing and motion during this time interval. Given the inherent difficulty of acquiring the image data at high enough speeds to reduce the likelihood and effects of patient motion, it can be understood that there will be advantages to methods that increase a detector's readout/process/transmit speed to allow faster image acquisition and processing, and thereby reduce the required scan time.

The discussion above is merely provided for general background information and is not intended to be used as an aid in determining the scope of the claimed subject matter.

BRIEF DESCRIPTION OF THE INVENTION

A computer implemented method for reconstructing a 3-D volume image using a radiographic imaging system having one or more x-ray sources and a digital detector. A plurality of radiographic images of a subject at various angles are captured in the digital detector. Image data in two or more pixels of the detector that are adjacent to each other in a row direction or a column direction are combined, while pixels adjacent in the other direction are not combined. An advantage that may be realized in the practice of some disclosed embodiments of the invention is reduced scan time.

In one embodiment, a computer implemented method for reconstructing a 3-D radiographic image of a subject is disclosed. The method uses a plurality of 2-D radiographic images of the subject captured by a radiographic imaging system having an x-ray source and a digital x-ray detector. At least one of the x-ray source and the detector is moved in a first direction to a plurality of imaging positions. A plurality of 2-D radiographic images of the subject are acquired each at one of the plurality of imaging positions. Captured image data in two or more pixels of the detector that are adjacent to each other in a direction parallel to the first direction are combined. A 3-D radiographic image of the subject is reconstructed using the acquired plurality of 2-D radiographic images. At least a portion of the reconstructed 3-D radiographic image may be displayed, stored, or transmitted to another site.

In another embodiment, a computer implemented method for tomographic image reconstruction uses a radiographic imaging system having one or more x-ray sources and a digital detector. A plurality of radiographic images of a subject are captured in the digital detector, including images at a plurality of positions during a relative motion as between the one or more x-ray sources and the digital detector. The relative motion is parallel to a row orientation of pixels in the detector or to a column orientation of the pixels in the detector. The radiographic images of the subject are read out from the detector, including combining captured image data in two or more pixels of the detector that are adjacent to each other in a direction parallel to the row orientation of pixels or to a column orientation of the pixels.

In another embodiment, a computer implemented method for tomographic image reconstruction uses a radiographic imaging system having one or more x-ray sources and a digital detector. In one step, a binning direction to be used to acquire radiographic images of a subject is determined. A plurality of projection images of the subject is captured in the detector including changing a relative angle as between the one or more x-ray sources and the subject for each captured projection image. The image data of each projection image captured in the detector is binned, or combined, in the determined binning direction to acquire the radiographic images of the subject. A tomographic image of the subject is reconstructed using the acquired radiographic images of the subject. The reconstructed tomographic image of the subject may be stored, displayed, or otherwise transmitted to another computing system.

An object of the present disclosure is to address the need for reduced exam time for computed tomography and digital tomosynthesis imaging. Embodiments of the present disclosure provide ways to increase the frame rate for image acquisition to help reduce image quality problems caused by patient motion during computed tomography and tomosynthesis exams.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a computer implemented method of reconstructing a 3-D image of a subject captured by an imaging system having an x-ray source and a digital x-ray detector. The system provides relative motion as between the x-ray source and the subject, and acquires digital radiographic images of the subject in the detector using asymmetric pixel binning. The detector includes multiple rows and columns of imaging pixels each capturing a digital image datum of each of the radiographic images. A 3-D image is reconstructed by processing the rows and columns of digital image data from the imaging pixels, including combining image data from pairs of row-adjacent or column-adjacent imaging pixels in the rows or columns of imaging pixels that are parallel to the direction of the relative motion of the source.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference may be made to the following detailed description, read in connection with the drawings in which:

FIGS. 10A-10B are schematic diagrams illustrating one exemplary method of asymmetric binning;

DETAILED DESCRIPTION OF THE EMBODIMENTS

Figure 1:
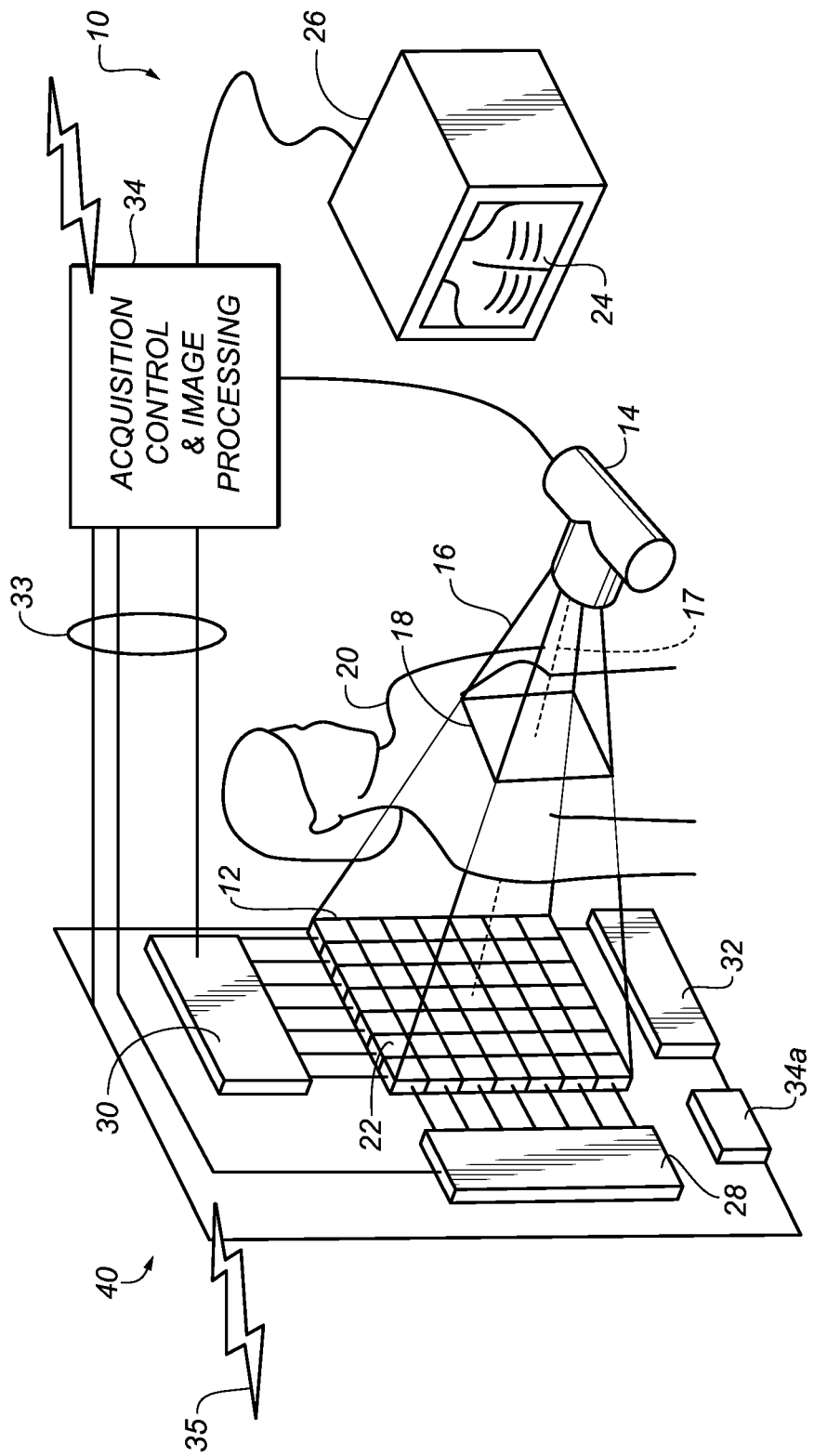
FIG. 1 is a schematic perspective view of an exemplary x-ray imaging system.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "modality" is a term of art that refers to types of imaging. Modalities for an imaging system may be conventional x-ray radiography, fluoroscopy or pulsed radiography, tomosynthesis, tomography, ultrasound, MRI, or other types of imaging. The term "subject" refers to the patient who is being imaged and, in optical terms, may be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

The terms "image" and "image data" may be used interchangeably in the context of the present disclosure. An image that is acquired by a digital imaging system contains data that may be processed, displayed, transmitted, and stored as image data.

For the image processing steps described herein, the terms "pixels" refers to picture image data elements, conventionally used with respect 2-D imaging and image display, and "voxels" for volume image data elements, often used with respect to 3-D imaging, and may be used interchangeably as the context indicates. It should be noted that the 3-D tomosynthesis image is itself synthesized from image data obtained as pixels in a 2-D sensor array and displays as a 2-D image at a particular viewing angle. Thus, 2-D image processing and image analysis techniques may be applied to the 3-D volume image data. In the description that follows, image processing techniques described as operating upon pixels may alternately be described as operating upon the 3-D voxel data that is stored and represented in the form of 2-D pixel data for display. In the same way, techniques that operate upon voxel data may also be described as operating upon pixels. With respect to an image detector, the term "pixel" may refer to a picture element unit cell containing a photo-conversion element and related circuitry for converting incident electromagnetic radiation to an electrical signal.

In the context of the present disclosure, "tomographic imaging" refers to volume radiographic imaging modalities such as computed tomography (CT) or tomosynthesis imaging. Tomographic imaging forms a volume 3-D image of a subject that may be viewed as a planar slice or plane section taken at a specified depth and angle. As noted previously, tomographic imaging obtains 3-D depth information by changing the relative angle between the x-ray source and the subject for each 2-D projection image that is acquired during scanning.

In the context of the present disclosure, the term "depth image" refers to a reconstructed tomographic image that represents depth information obtained from processing multiple 2-D images or projection images of the subject, taken from different angles. Depth images obtained from tomosynthesis do not typically provide full 3-D representation; depth images obtained from 360° computed tomography (CT) scans provide more complete 3-D depth information. The noun "projection" may be used herein to mean "projection image", referring to one of the 2-D images that is captured and processed to reconstruct a depth image.

In the context of the present disclosure, the term "aspect ratio" has its conventional meaning as related to two-dimensional polygons and other shapes and generally relates height to width in 2-D space. Thus, for example, two squares of different size exhibit the same aspect ratio. Two rectangles may or may not have the same aspect ratio. It should also be noted that a square is considered a special case of rectangular shape with equal sides. Aspect ratios are considered to differ from each other if the ratio between the two varies by more than about 10%, preferably less than 10%.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. However, in a tomographic or tomosynthesis succession of image captures (scan) the perpendicular relation may not be maintained or desired due to relative movement as between the source 14 and the detector 40. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed, or read out, by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be read out one or more at a time using electronic gate driver circuit 28 so that the exposure data from the array 12 may be transmitted to electronic read out circuit 30, which read out circuit may include amplifiers and analog-digital converters, as described herein. In certain embodiments disclosed herein, relative placement of the readout hardware (vertically or horizontally), including gate driver circuit 28 and the electronic read out circuit 30, may be used to determine a preferred binning direction, such as binning in the direction toward the read out circuit 30, for example. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, which may be referred to herein as a pixel value, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing unit 34 functions may reside in the detector 40 in an on-board processing system 34a which may include a processor and electronic memory to control operations of the DR detector 40 as described herein, including control of circuits 28, 30, and 32, by use of programmed instructions, and to store and process image data similar to the functions of standalone acquisition control and image processing system 34. The image processing system 34, 34a, may perform image acquisition and image disposition functions as described herein. The image processing system 34a may control image transmission and image processing and image correction on board the detector 40 based on instructions stored therein or in response to commands transmitted from the acquisition control and image processing unit 34, and may transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
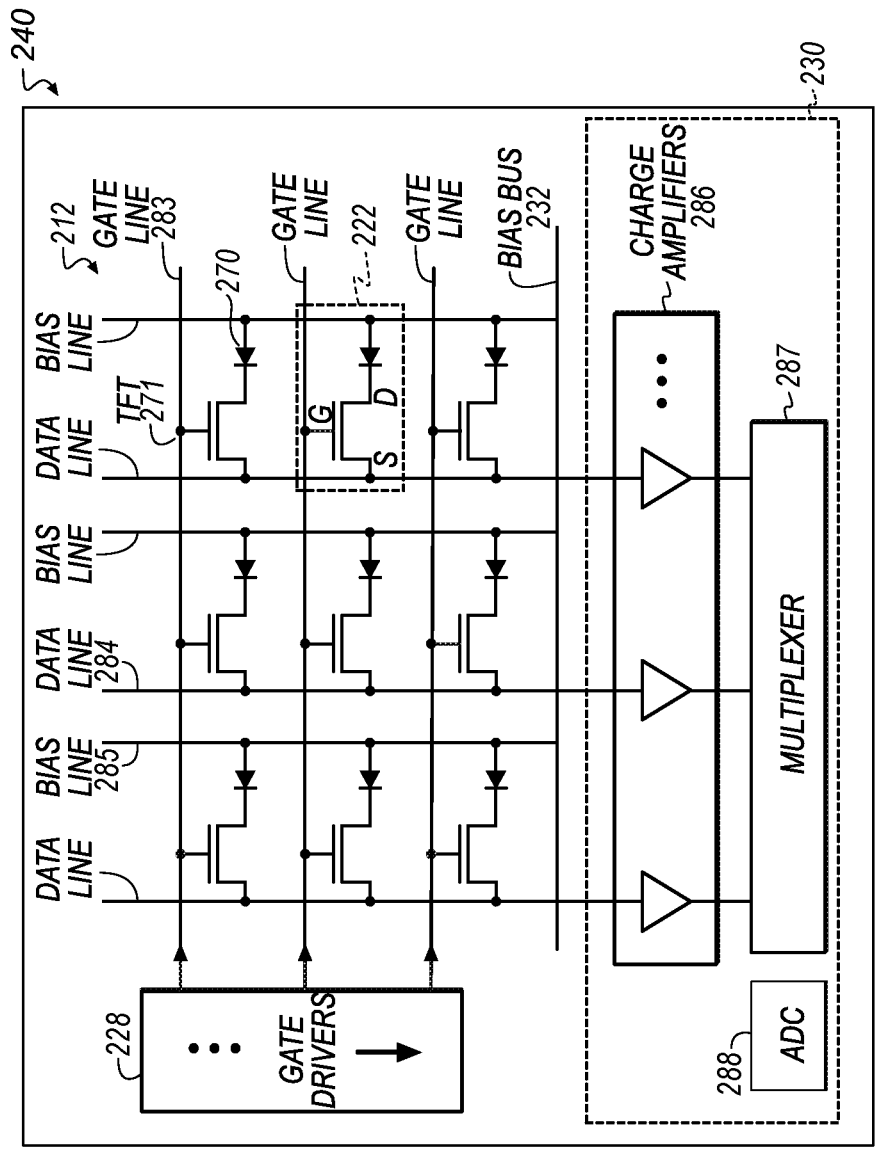
FIG. 2 is a schematic diagram of a photosensor array in an exemplary digital radiographic (DR) detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photo sensor cells 12 may be formed in a device layer that abuts adjacent layers of the DR detector structure, which adjacent layers may include a rigid glass layer or a flexible polyimide layer without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34, 34a, to yield a digital image which may then be digitally stored and immediately displayed on monitor 26, or it may be displayed at a later time by accessing the digital electronic memory containing the stored image. The DR detector 40 having an imaging array as described with reference to FIG. 2 is capable of both single-shot (e.g., static, radiographic) and continuous (e.g., fluoroscopic) image acquisition.

Figure 3:
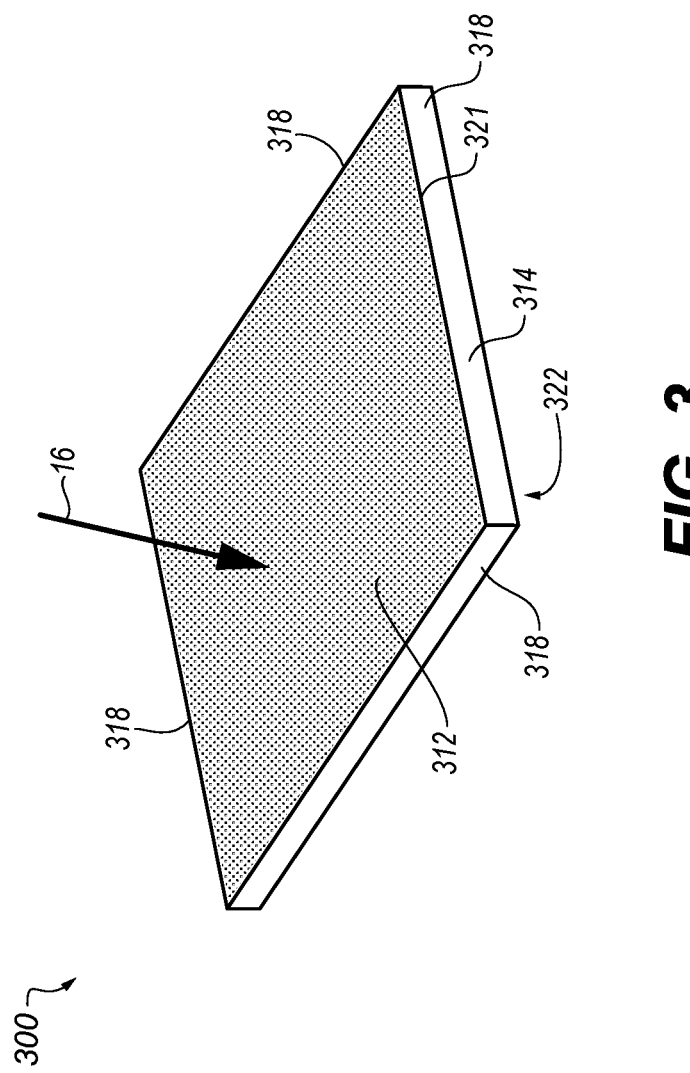
FIG. 3 is a diagram of an exemplary DR detector.

FIG. 3 shows a perspective view of an exemplary generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
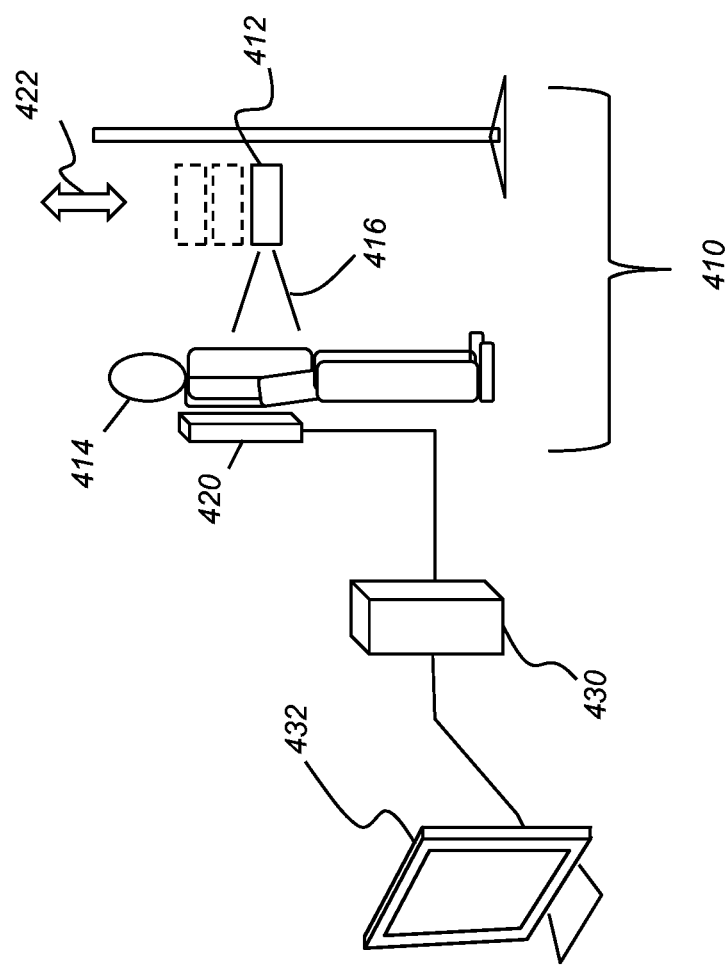
FIG. 4 is a schematic diagram that shows exemplary components of a tomosynthesis imaging system that performs a vertical exam.
Figure 5:
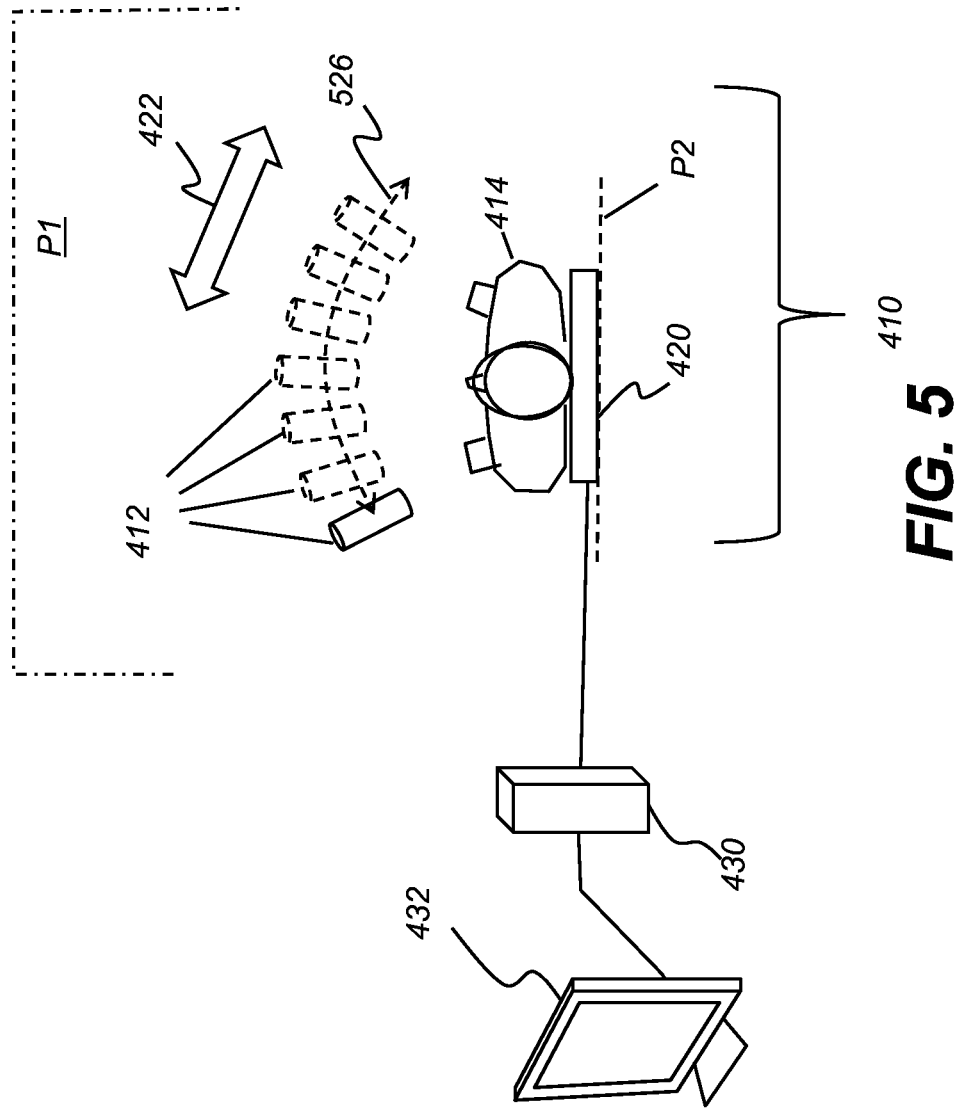
FIG. 5 is a schematic diagram that shows exemplary components of a tomosynthesis imaging system that performs an arcuate scan.

Referring to the schematic diagrams of FIGS. 4-5, there is illustrated a tomosynthesis imaging system 410 having an x-ray source 412 that directs imaging radiation 416 toward a detector 420 that captures images of a subject 414 positioned therebetween. Detector 420 may be in signal communication with a host processor 430, such as an external computer or dedicated processor, for example, that processes the image data obtained by the imaging system 410. Processor 430 is in signal communication with a display 432 for displaying the processed, reconstructed volume image of the subject 414. Processor 430 may also store the reconstructed volume image data in an electronic memory or transmit the image data to another computer system, for example. To capture image depth information of the subject 414, X-ray source 412 may be moved along a curved or linear path 422, such as a linear vertical path of travel as shown in the example of FIG. 4. For a subject 414 in a prone position, X-ray source 412 may be moved in a curved or linear horizontal direction.

Other paths of travel may also be non-linear, such as the arcuate path of travel shown in the schematic diagram of FIG. 5. Here, the motion direction 422 is along an arc 526 in a plane P1 that is orthogonal to the plane P2 of the detector 20. In both vertical and prone subject orientations and where relative motion as between source 412 and detector 420 is in an arcuate pattern as shown in FIG. 5, motion direction 422 of the x-ray focal spot may be along a line that lies in a plane P1 that is perpendicular to a plane P2 of the detector 420.

Figure 6:
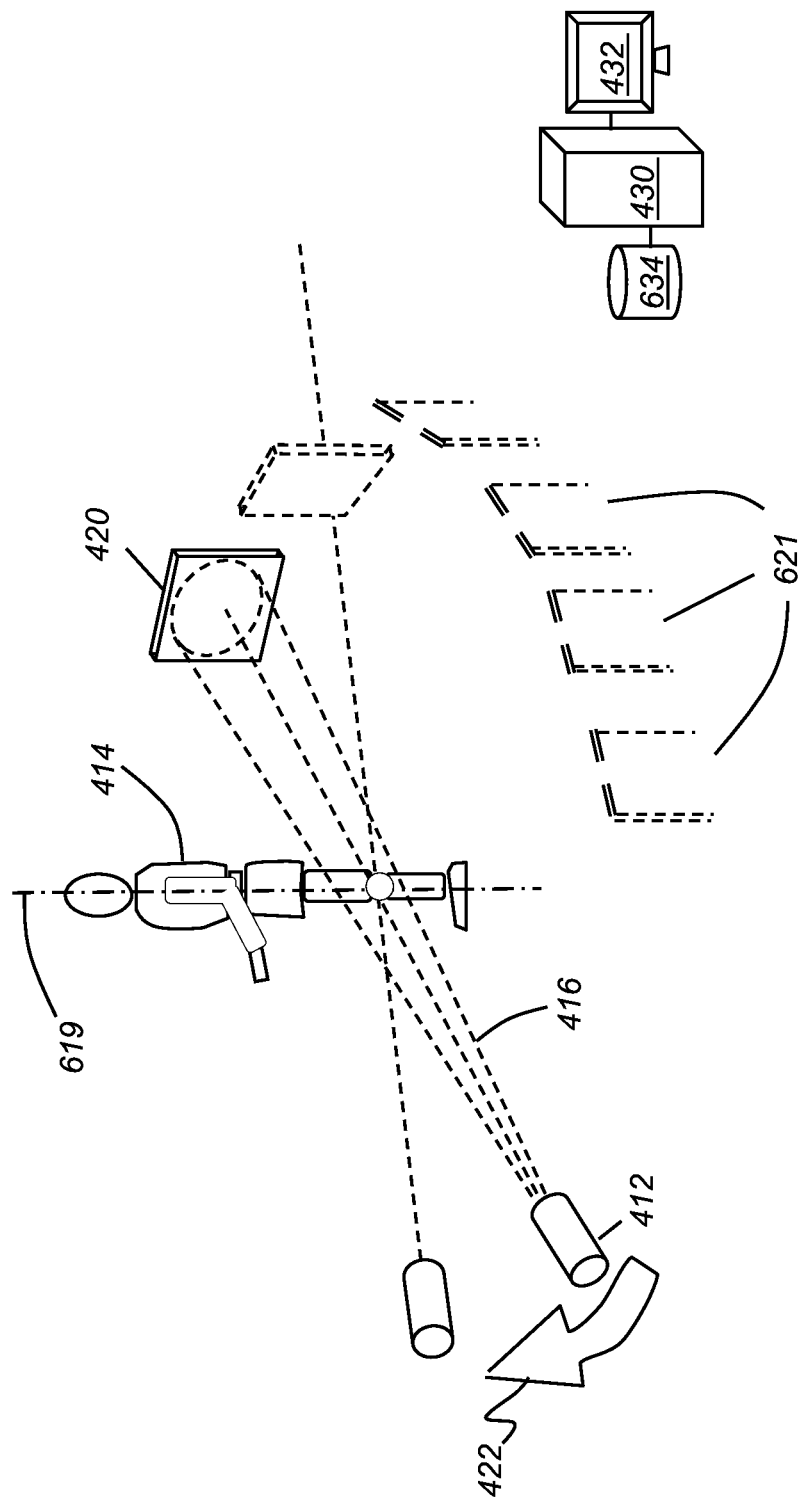
FIG. 6 is a schematic diagram that shows an exemplary computed tomography imaging system used for image acquisition and processing.

Referring to the perspective view of FIG. 6, there is shown, in schematic form a conventional cone-beam computed tomography (CBCT) imaging system for obtaining individual 2-D images of subject 414 that are used to form a 3-D volume image of the subject 414. A cone-beam radiation source 412 directs a cone of x-ray radiation 416 toward the subject 414 and detector 420. A plurality of 2-D images of the subject 414 are captured in the detector 420 in succession at varying angles about the subject 414, such as one image captured at each 1-degree angular increment, as the source 412 and detector 420 revolve about a central imaging axis 619 along an arc in a direction 422. The subject 414 is preferably placed at or near the central imaging axis 619 during the imaging procedure. FIG. 6 shows a representative sampling of DR detector 420 positions 621, corresponding to diametrically opposed positions (not shown) of the source 412, to illustrate how these images are obtained relative to the position of subject 414 at or near the central axis 619. Once the needed 2-D projection images are obtained in this sequence, a suitable imaging algorithm processes the 2-D images to generate the 3-D volume image of the subject 414. Image acquisition and program execution may be performed by a computer processor 430 that is in wired or wireless communication with DR detector 420, or the image processing may be performed by an on-board processing system 34a (FIG. 1) as described herein. Processed images may be stored in computer-accessible memory 634 and the 3-D volume image data may be stored, transmitted over a network, and/or presented on a display 432.

Figure 8:
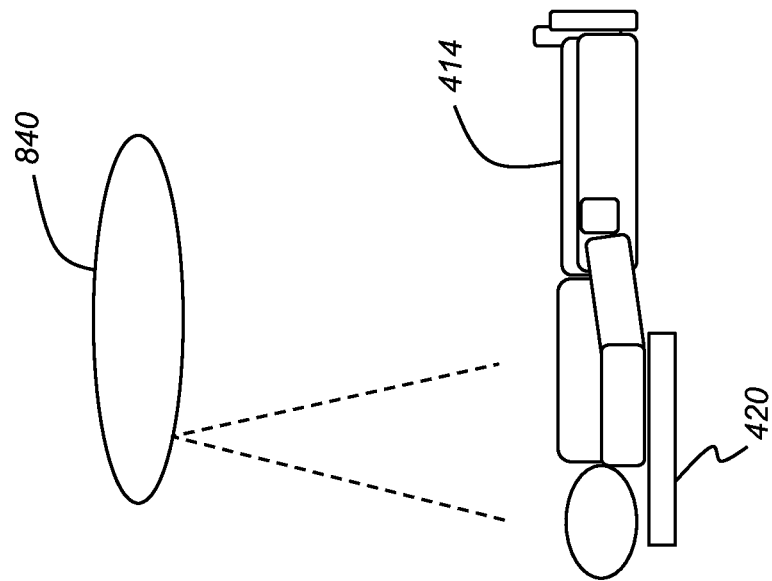
FIG. 8 is a schematic diagram that shows another exemplary array of x-ray sources that may be arranged to direct radiation toward the patient from different angles.
Figure 7:
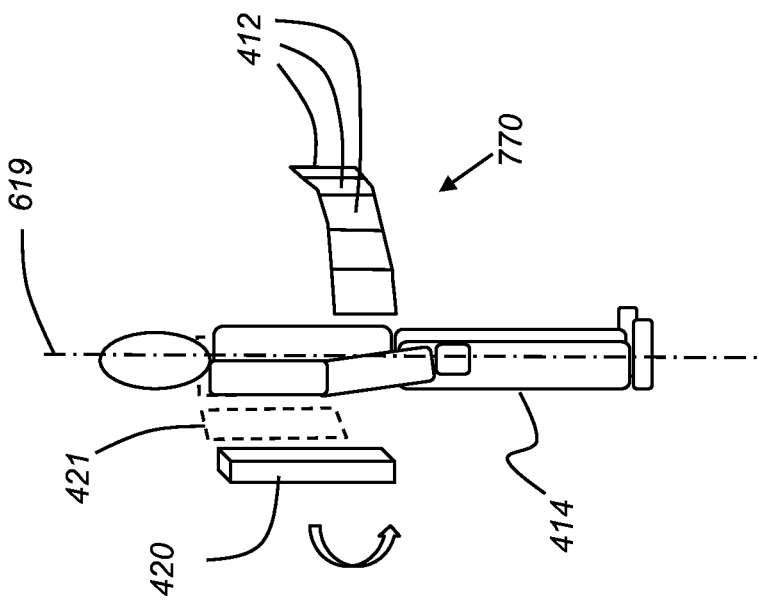
FIG. 7 is a schematic diagram that shows an exemplary tomographic imaging system using an array of x-ray sources.

FIG. 7 is a schematic diagram that shows a tomographic imaging system having an array 770 of stationary x-ray sources 412 and a movable detector 420 that moves about a central axis 619 to positions, e.g., position 421, diametrically opposite, in relation to central axis 619, to individually energized x-ray sources in the array 770. The x-ray source array 770 may include carbon nanotubes (CNT) or other types of x-ray emitters designed to be fired in a programmed sequence to change an exposure angle of x-ray energy through the subject 414 toward detector 420 to obtain each 2-D projection image. FIG. 8 is a schematic diagram that shows another curved pattern 840 in which an array of x-ray sources 770 may be arranged to direct radiation toward the patient 414 and the detector 420 from different imaging angles.

As may be appreciated by those skilled in the image processing arts, a computer program for iterative volume image reconstruction may be utilized by a suitable, computer system 430 or processing systems 34, 34a, including personal computers, workstation, and on-board processors, that act as an image processor under program control to acquire, process, and display data as described herein. Many other types of computer systems architectures may be used to execute a computer program of the present disclosure. To increase a frame rate of a digital detector used for tomographic imaging, in general, and for tomosynthesis in particular, the applicants disclose herein a method using asymmetric binning of the image data captured in individual pixels of the digital detector.

Figure 9:
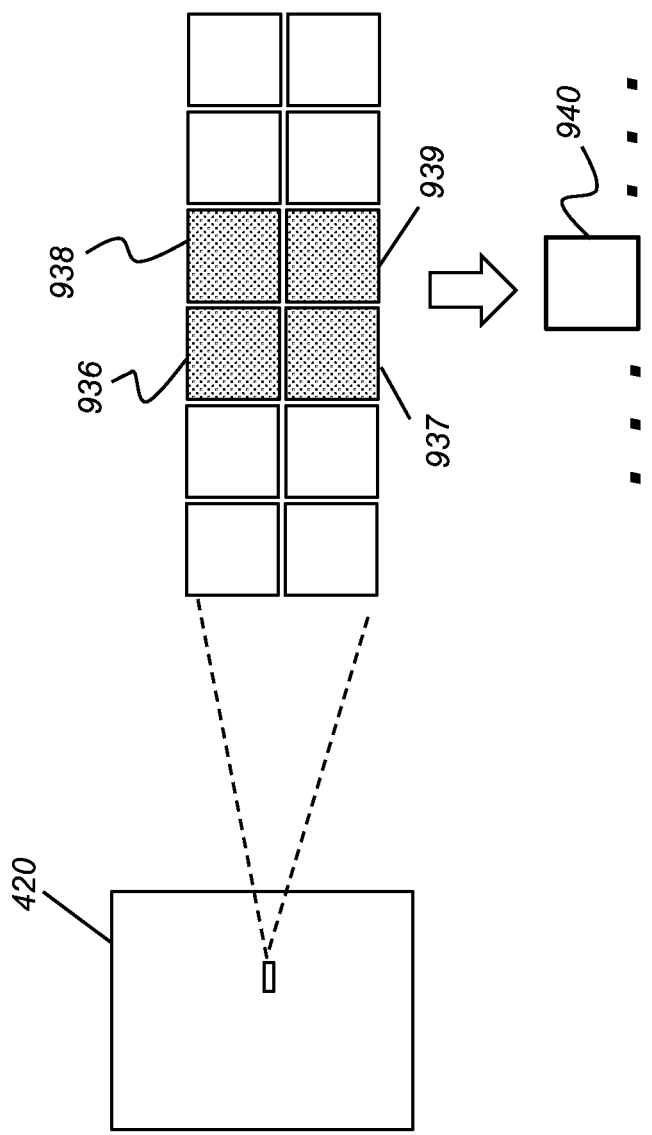
FIG. 9 is a schematic diagram illustrating one exemplary method of symmetric binning.

Symmetric pixel binning, in which image data captured in multiple imaging pixels is grouped, or combined, in order to provide a single pixel value representing the group of pixels, is known. FIG. 9 shows, using a portion of adjacent imaging pixels from two rows of detector 420 as representative imaging pixels, how conventional pixel binning combines pixel values captured in adjacent imaging pixels such that a 2×2 arrangement of adjacent imaging pixels 936-939, is represented by a single imaging pixel value 940. In the schematic diagram of FIG. 9, pixel values captured in column and row adjacent imaging pixels 936-939 are combined and stored as a single pixel value such as a binned pixel value 940. Using conventional 2×2:1 pixel binning, the resulting amount of captured image data available for providing image resolution is ¼ that of the original image because the binning ratio is 4:1. It may be appreciated that this level of resolution reduction may be of benefit for subsequent transfer time, processing time, and signal-to-noise ratio. However, conventional binning defeats the purpose of high-resolution diagnostic imaging and reduces the overall diagnostic value of the acquired image content.

An asymmetric binning method disclosed herein applies a pixel binning process that is more pronounced in one direction than in a direction orthogonal thereto, so that pixels are binned in a 2:1, or 1:2 ratio, for example, (e.g., representing row:column order) representing an embodiment wherein pairs of adjacent pixels in each row or column, but not both, of the detector 420 are combined into one pixel value, so that the resolution along the row direction or column direction is reduced by half and each column or row, respectively, is read at full resolution. The schematic diagram of FIG. 10A shows a column binning 1:2 arrangement, in which each row pixel combines two pixel values captured in adjacent pixels in a vertical (column) direction. Referring to the schematic diagram of FIG. 10A, a 1:2 binning of the present disclosure is shown for a block of pixels similar to that shown in FIG. 9. Detector pixels 936, 937, which are adjacent in a vertical column direction 1028 are binned to provide a single common pixel value 941 representing pixel values 936, 947, while providing full resolution in the row direction 1027, e.g., values of pixels 936 and 938, or 937 and 939, are not combined. Similarly, column adjacent detector pixels 938 and 939 are binned, or combined, to provide a single common pixel value 942 in the column direction. In one embodiment, the single combined pixel value 941 may be equal to an average pixel value of the binned pixels 936, 937, and the single combined pixel value 942 may be equal to an average pixel value of the binned pixels 938, 939.

FIG. 10B illustrates a schematic diagram representing a slightly larger portion of an array of pixels in a detector 420, as compared to FIG. 9, to further illustrate the embodiment of 1:2 pixel binning. As described with reference to FIG. 9, FIG. 10B illustrates the pixel values of unbinned column adjacent pixels 936, 937, are combined into the binned pixel value 941; the pixel values of unbinned column adjacent pixels 938, 939, are combined into the binned pixel value 942; the pixel values of unbinned column adjacent pixels 943, 944, are combined into the binned pixel value 947; and the pixel values of unbinned column adjacent pixels 945, 946, are combined into the binned pixel value 948, and so on for the entire image frame. The resulting stored array of combined pixel values, shown on the right side of FIG. 10B, provides the same resolution in the horizontal (row) direction as the unbinned pixels on the left of FIG. 10B, i.e., six pixel values, while the resolution in the vertical (column) direction is reduced by one-half, i.e., six unbinned pixels in the column direction are reduced to three pixels in the column direction. Asymmetric binning may use any suitable pairing or grouping arrangement, including 2:4, 4:2, 6:1, 6:2, and so on, and may use any appropriate pixel value calculation to determine the pixel values of the binned pixels to representing the original unbinned pixel values. In asymmetric binning, the larger number indicates whether the row or column (row:col) direction is predominant or, expressed alternatively, the larger number indicates whether the image data in the corresponding row or column has coarser resolution than the row or column corresponding to the smaller number.

Among factors that may be used to determine the predominant binning direction, e.g., vertical (column-wise binning) or horizontal (row-wise binning) are the following:

(i) Detector hardware characteristics. Due to design of the gate driver and readout hardware of the digital detector, it may be more efficient to bin pixels along one direction than along the orthogonal direction. Binning of 2, 3, 4, or more pixels along the row may be more readily accomplished than binning of any number of pixels in the column direction, simply according to a design of the pixel readout components, which may include gate driving circuitry connected to rows of imaging pixels, and read out circuitry connected to columns of pixels, for example. In one embodiment of a column-wise binning, the gate driver circuitry may be programmed to read out two rows of the detector array simultaneously, such that the accumulated read values per column may be divided by two to determine the combined, binned (average) pixel value for each two adjacent column pixels, similar to the embodiments described herein in relation to FIGS. 10A-10B. Similarly, in a 1:3 binning embodiment, the gate driver circuitry may be programmed to read out three rows of the detector array simultaneously, such that the accumulated read values per column may be divided by three to determine the combined, binned (average) pixel value for each three adjacent column pixels. In one embodiment of a row-wise binning, the read out circuitry may be programmed to combine and average every two row-adjacent pixel values of the detector array, such that the discrete pixel values stored per row are reduced as the average value is stored to represent each pair of row-adjacent pixels.

(ii) Pixel aspect ratios. The photosensor area of each imaging pixel in a detector may not be symmetric, such as having a greater length or width dimension, for example. A pixel's photosensor aspect ratio asymmetry may make it more useful to apply binning in one direction than in its orthogonal direction.

(iii) Direction of scanning motion and motion blur. The binning direction may be selected based on the direction of relative x-ray source and/or detector motion or position change, such as binning the column or row adjacent pixels that are parallel to a motion direction of the source and/or the detector of an imaging system.

(iv) Type of image and scanned anatomy. The type of image to be obtained may be used to determine the predominant binning direction for asymmetric binning, as described herein.

In computed tomography, both the x-ray source and the digital detector revolve about a subject under examination. In tomosynthesis, the detector may be stationary, the detector may move in a direction opposite to the x-ray source movement for a linear scan path, or the detector may simply rotate to constantly face the x-ray source in an embodiment wherein the source moves along a linear or an arcuate path.

In one embodiment, a stationary array of smaller x-ray sources such as a carbon nanotube (CNT) array may be used to obtain a plurality of images of a subject at varied angles instead of a single moving x-ray source. Such a CNT array may include a plurality of individually energizable x-ray source elements arranged along a line, an arc, a curve, a circle, or other desired geometric arrangement. Successive energization of selected ones of the sources in the CNT array under programmed control, each energization to capture a 2-D image of a subject, may effectively emulate various motion patterns and imaging positions of a single source as described herein.

For many of the tomography modes described herein, with respect to the detector 420, a relative motion direction 422 of the x-ray source's focal spot, which may be relative to the subject under examination or relative to a stationary detector, approximately corresponds to either of two orthogonal directions: (i) the direction 1027 that is parallel to the rows of pixels in the detector 420 or (ii) the direction 1028 that is parallel to the columns of pixels in the detector 420.

For either computed tomography or for tomosynthesis, the x-ray exposure time (energization) per projection image is very brief, e.g., about 5 ms, and the x-ray source is thus typically briefly pulsed in order to expose the subject for each projection image. With a brief pulse energization of the x-ray source, there is inherently some amount of a motion blur artifact that is introduced into the image captured at the detector because of the change of position of the x-ray source with regard to the subject being exposed. The amount of motion blur is asymmetric and typically more pronounced in either the row direction or column direction in the detector based on the direction of relative motion as between the source and detector. Thus, the image motion blurring is asymmetric with blurring parallel to the source motion direction and with no perceptible blurring in the direction that is orthogonal to source motion.

The continuously changing position of the x-ray source with respect to the subject may be addressed by a digital image processing method including pixel binning in a direction parallel to the path of relative x-ray source motion with respect to the subject being imaged. Using a 2:1 pixel binning method with the predominant factor ("2") parallel to the direction of x-ray source motion, the binning method disclosed herein reduces the overall amount of a frame of image data by one-half, with the coarser resolution being obtained in the direction of image blur, i.e., parallel to the relative motion direction. As used herein, a frame of image data is the amount of data captured by imaging pixels in an area of a digital detector that is exposed to x-ray imaging radiation, which may include the entire pixel array of the detector or a portion of the pixel array, such as if the exposed image area is collimated. As a result of applying an asymmetric binning process to the imaging pixels of the detector's array of pixels, the inherent image blur is less perceptible. Full resolution is obtained in a direction orthogonal to the relative x-ray source motion which may result in no observable image blur. Following the pattern outlined above as described with respect to FIG. 10A, and using 1:2 binning, half of the unbinned pixel data in the motion direction 422 is generated. Thus, resolution in the motion direction 422 is reduced by half because the pixel values as captured in two exemplary adjacent pixels 936, 937, is combined into one common pixel value 941. The resolution obtained by pixels 936, 938, in a direction 1027 orthogonal to column-wise motion direction 422 retains the native resolution of the detector.

Referring again to the schematic diagram of FIG. 10A, 1:2 binning may be applied to pixels 936, 937, that are adjacent in a direction parallel to relative motion direction 422. Motion direction 422 may be referred to as vertical (parallel to column orientation 1028) for this illustrated configuration, so that image blur would tend to be more noticeable in the vertical direction. As described previously, detector pixels 936 and 937 are binned to provide a read pixel 941; detector pixels 936 and 939 are binned to provide a read pixel 942. Following this same pattern across all exposed pixels in the detector 420, the binning method disclosed herein may be used to generate an amount of image data comprising half of the amount of image data capable of being captured in the imaging pixels oriented in the direction of motion 422. Resolution in the motion direction 422 may be reduced by some other factor, such as by 3:1 or more, based on the binning parameters that are applied. Resolution orthogonal to motion direction 422 may remain the same as the native pixel resolution of the detector. Using the binning method disclosed herein, the impact of binning on image resolution and overall image quality may be limited as there is inherently at least some amount of blurring along the direction of motion and, in practice, the binning method disclosed herein may not introduce additional resolution loss.

Figure 11:
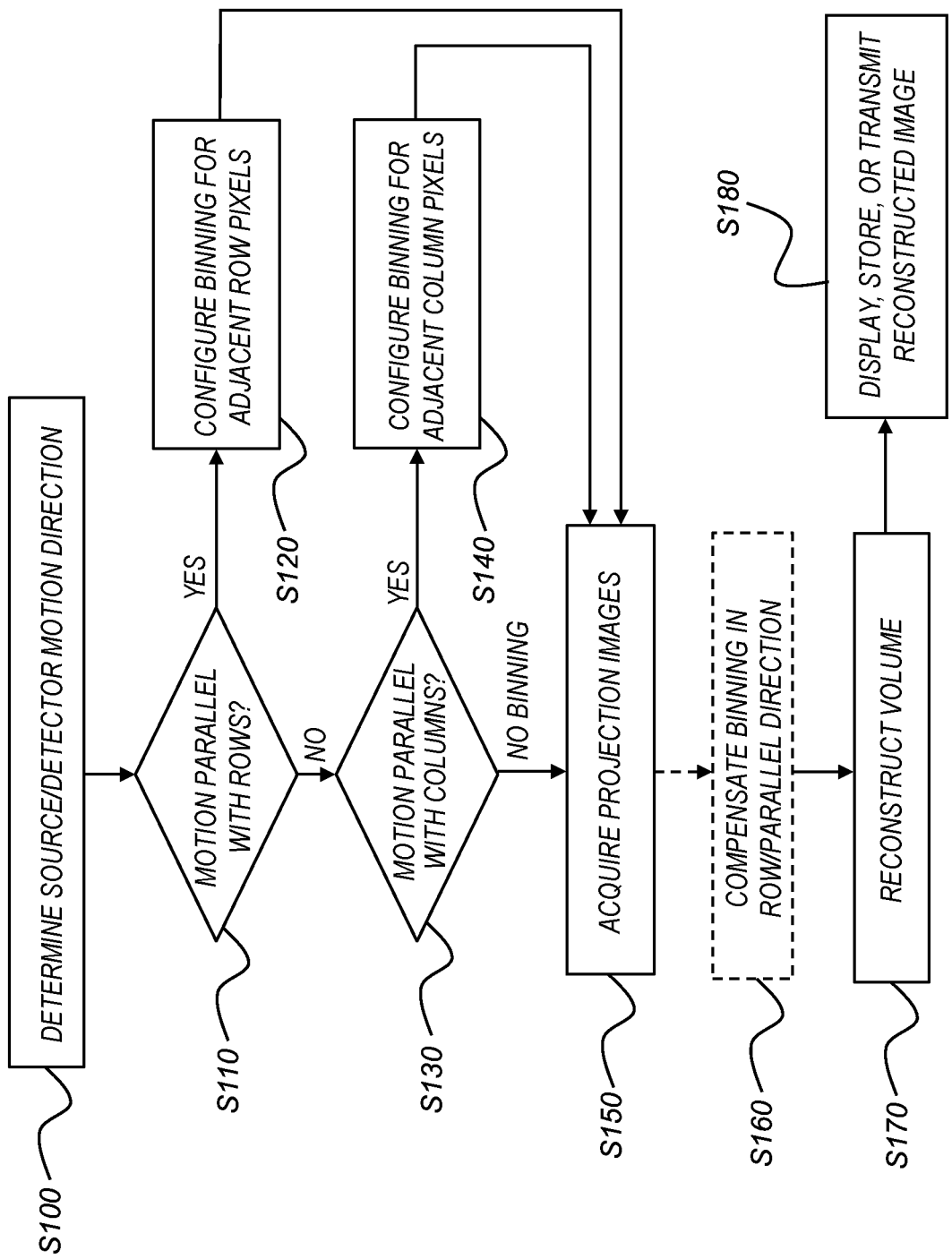
FIG. 11 is a flow diagram illustrating an exemplary tomosynthesis volume image reconstruction method using asymmetric binning according to an exemplary embodiment of the present disclosure.

The logic flow diagram of FIG. 11 shows a sequence of automated steps for tomosynthesis image acquisition and processing using asymmetric binning for detector columns or rows according to an embodiment of the present disclosure. These steps may be executed, for example by an appropriately programmed host processor 30 in the configuration of FIGS. 4-6, for example. In a determination step S100, the imaging system configuration is identified to determine the relative motion direction of the source to determine what binning direction is applied. The imaging system arrangement may be determined from the imaging system setup, which may be input to the imaging system by an operator, such as by a configuration switch setting, or other suitable input signal. A decision step S110 then determines whether or not the motion direction is parallel to pixel rows of the detector, and thereby perform a row binning configuration step S120 where motion will be applied in the row direction. If the motion direction is determined not to be in the row direction at step S110, a second decision step S130 then determines whether or not the motion direction is parallel to pixel columns of the detector and performs a column binning configuration step S140 where motion will be applied in the column direction. Where row binning, column binning, or neither, are applicable, the image acquisition process continues at step S150 to acquire the projection images with the appropriate row or column binning, or neither, applied.

Continuing with the logic flow of FIG. 11, if asymmetric binning has been applied, the imaging system, in an alternative compensation step S160, may apply further image processing to the acquired image in order to restore at least some portion of the original image resolution. This may improve, for example, the reconstruction processing that follows, since reconstruction with asymmetric input may benefit from a resolution adjustment of the input image data. A reconstruction step S170 then uses the acquired images from steps S150 or S160 to generate volume image data. A display step S180 then executes to display, transmit, or store the reconstructed tomosynthesis image. Other post processing functions may also be executed, including the use of super-resolution techniques to attempt to recover some portion of the original image resolution.

The exemplary embodiments disclosed herein may address the need for reduced image processing time and improved detector frame rate in computed tomography and in digital tomosynthesis by an asymmetric pixel binning process that reduces the amount of data to be processed per captured image frame. Asymmetric binning may be applied in a predominant direction, based on optimization factors selected by the user. Acquiring image content for binning may include firing the source for about 5 ms for each radiographic image exposure. Asymmetric binning may operate by combining the image data from more than two row-adjacent or two column-adjacent imaging pixels and determining an average per pixel of the combined image data.

For reconstructing the volume image from the 2-D projection data, the reconstruction algorithm may take a number of approaches to binned image data from the detector. The reconstruction algorithm may be adapted to using asymmetrically binned image data or an up-sampling of the binned image data may be applied, potentially compensating for some component of the reduced resolution in the binning direction. Post processing of the reconstructed images to compensate potential resolution loss may be required, such as to sharpen the 3-D volume image. The sharpening may be performed in the direction of the motion in a one-dimensional process, or using a two-dimensional process for image slices.

Figure 13:
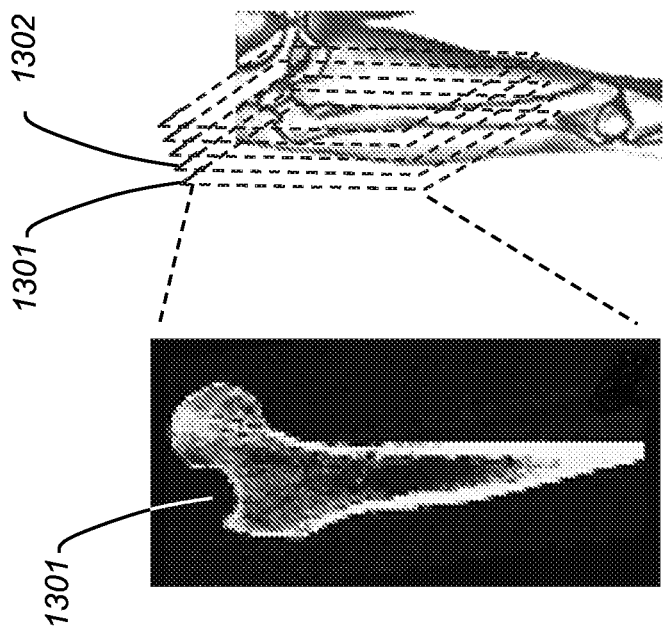
FIG. 13 shows an image of an exemplary horizontal slice of a femur.
Figure 12:
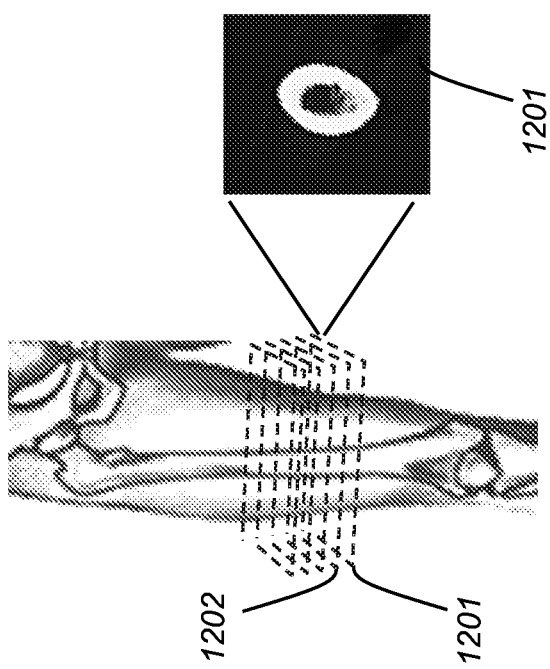
FIG. 12 shows an image of an exemplary vertical slice of a femur.

For some types of tomographic imaging, the predominant binning direction may be guided by an anatomy of the subject. This may apply where anatomical structure tends to vary in a first direction rather than in a second direction, which may be orthogonal to the first direction. For example, when imaging a femur, its bone structure extends along a length dimension of the leg, such as in a vertical direction for a person standing upright. Referring to FIGS. 12 and 13, as illustrated there is only a small amount of change from one horizontal cross-section 1201 to the next 1202. By comparison, vertical cross-sections 1301, 1302, taken through the same anatomy may vary considerably from each other. This relative change in cross-sectional image data may be used to select a binning direction regardless of a relative motion direction as between the source and detector as described herein. Following such examples of different anatomical characteristics, binning direction may be selected wherein coarser, reduced resolution is less perceptible. Thus, for the example of the femur in FIGS. 12-13, binning in the vertical direction, which results in a reduced resolution for the horizontal slices 1201, 1202, is less noticeable than a binning applied in the horizontal direction which would result in a reduced resolution for the vertical slices 1301, 1302.

To determine a binning direction to be applied in a radiographic imaging procedure, a look-up table (LUT) may be stored in the imaging system that indexes exam types or anatomical identifiers to preferred binning directions. Using the example shown in FIGS. 12-13, an instruction to acquire a volume image of the femur for a standing patient would initialize the imaging system for binning in the vertical direction, to provide coarser resolution for projection data acquired in the vertical direction and full resolution in the horizontal direction.

In one embodiment, wherein the detector may indicate a preferred binning direction due to its hardware configuration, such as where binning along rows may process images faster than binning along a column direction, for example. Such a hardware configuration effect may be based upon which direction in the detector the gate drivers are positioned versus the data line read out circuitry and the processing steps that are performed thereby. An instruction may be stored in the detector to output an indication identifying a preferred orientation of the detector for a binning procedure. The generated indication may cause instructional text to be displayed on a monitor, for example, or a symbol on a monitor to inform an operator of the imaging system. Where the detector is attached to an apparatus that automatically controls an orientation of the detector, such as rotating the detector in increments of 90 degrees, for example, an instruction may be generated to cause an actuator to adjust the detector orientation automatically. As described herein, a binning direction may be selected based on subject anatomy, based on relative motion direction of the x-ray source, or on a detector hardware configuration, including positioning of read out circuitry or asymmetric photosensor dimensions.

Figure 14:
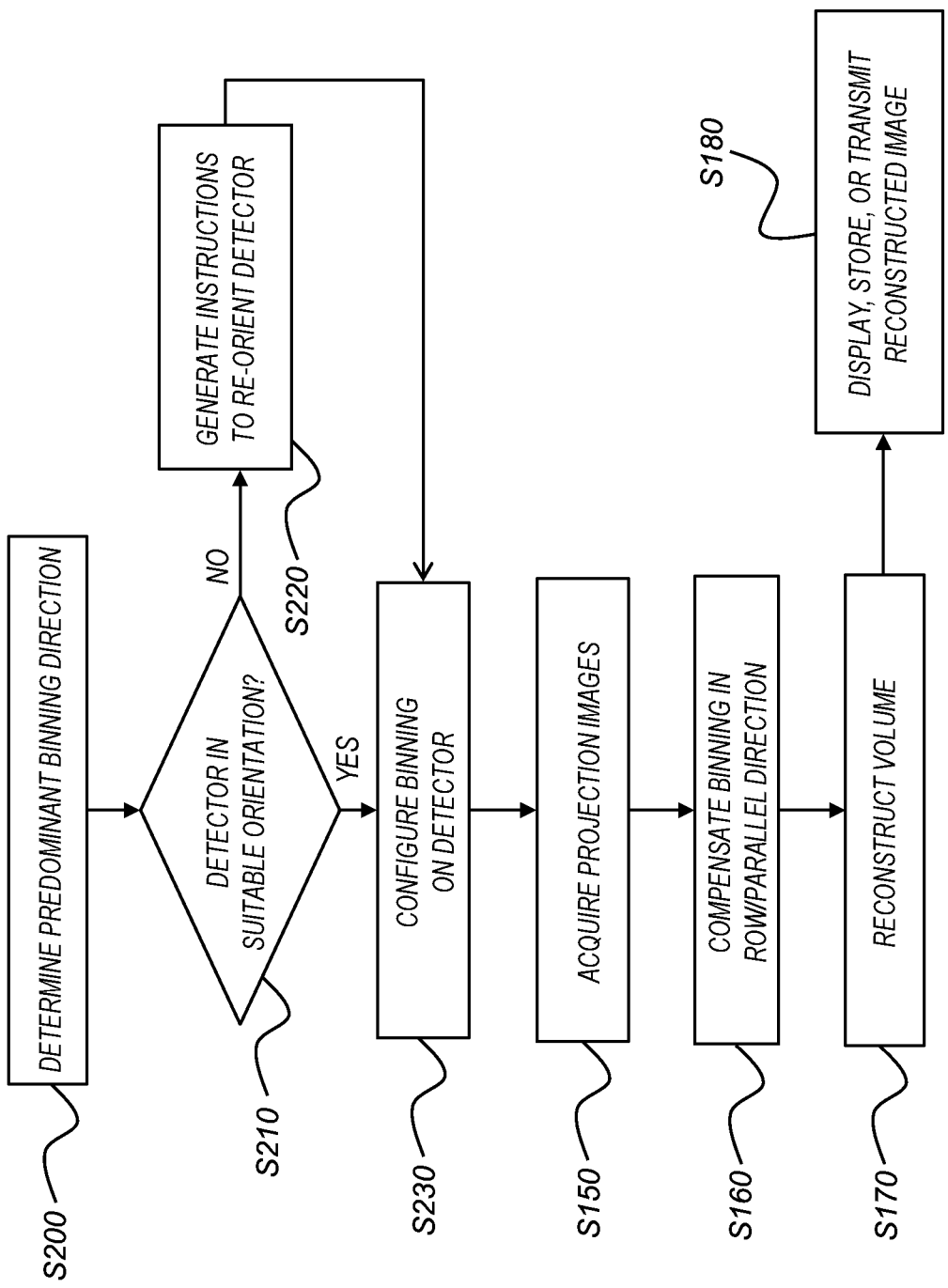
FIG. 14 is a logic flow diagram illustrating an exemplary method for imaging using binning according to an exemplary embodiment of the present disclosure.

The logic flow diagram of FIG. 14 shows a sequence for imaging using binning according to one embodiment of the present disclosure. In a determination step S200, the preferred or predominant pixel binning direction is ascertained according to any of the criteria described herein, or other criteria. Presets, such as those stored in a LUT, may be selected and stored by operators at an imaging facility or factory stored settings may be used. Briefly summarized, the predominant binning direction may be set according to (i) detector hardware; (ii) photosensor aspect ratios; (iii) motion blur; or (iv) type of image or scanned anatomy. Where the type of anatomy determines the predominant binning direction, this information may be obtained in a number of ways. An LUT may be used for the exam type, as described previously. Alternately, a scout image may be obtained as a check on anatomy orientation prior to scanning as well as to ascertain the orientation of the detector where there is already an inherent hardware asymmetry. A scout image may be obtained as a low-dose image of the subject.

Continuing with the FIG. 14 sequence, an optional orientation check step S210 then determines whether or not the detector is at the preferred orientation for binning operation. If the detector may be better positioned, as determined by control logic, an instructions generation step S220 executes, providing a displayed or audible instruction to the operator or, for an automated system, providing a signal to an actuator that performs a re-orientation of the detector. A subsequent detector configuration step S230 then configures the detector for binning operation. Logic flow is then similar to the sequence shown in FIG. 11. Projection image acquisition step S150 acquires the projection images with the appropriate row or column binning applied. Optional compensation step S160 applies further image processing of the acquired image in order to restore at least some portion of the original image resolution. Reconstruction step S170 then uses the acquired images from steps S150 and S160 to generate volume image data. Display step S180 then executes for display, transmission, or storage of the reconstructed tomosynthesis image. Other post processing functions may also be executed, including the use of super-resolution techniques to attempt to recover some portion of the original image resolution.

Figure 15:
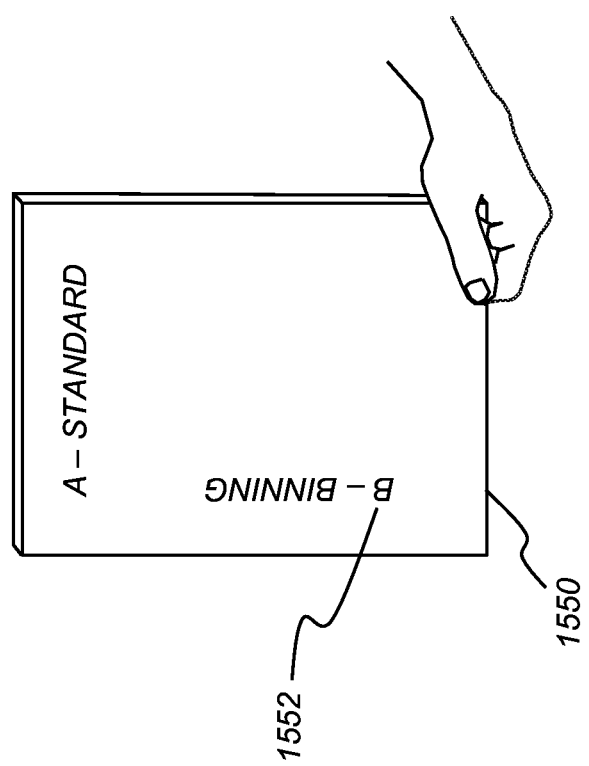
FIG. 15 is a schematic diagram illustrating a detector with indicia to indicate a binning direction.

In one embodiment, a digital detector may be provided that includes markings indicating a preferred binning direction based on detector hardware. Indicia on the detector cover or along an edge of the detector may show the direction in which binning, if selected by an operator, will automatically be executed. The schematic diagram of FIG. 15 shows an example of a detector 1550 with indicia 1552 to show a binning direction oriented according to a detector hardware characteristic.

Binning may also be changed from one projection image to the next, based on what type of resolution is most useful from a particular angle. In some cases, no binning may be applied for images that capture fine detail in both row and column dimensions, with increased binning as the radiation direction changes from that position. For an embodiment using an array of sources, binning may even change direction from one image to the next, based on changes in an exposure angle. For exemplary functions described herein and/or performed as described with reference to the figures, the system processor, host computer or the radiographic imaging system/unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), GPU, video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

Consistent with embodiments described herein, a computer program with stored instructions may be used that controls system functions for image acquisition and image data processing for image data that is stored and accessed from an electronic memory. As may be appreciated by those skilled in the image processing arts, a computer program of an embodiment of the present invention may be utilized by a suitable, general-purpose computer system, such as a personal computer or workstation that acts as an image processor. However, many other types of computer systems may be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, may refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer may also be considered to be a memory, as the term is used in the present disclosure. Memory is also used as the data workspace for executing and storing intermediate and final results of calculations and other processing. Computer-accessible memory may be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications may be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A computer implemented method for reconstructing a 3-D radiographic image of a subject using a plurality of 2-D radiographic images of the subject captured by a radiographic imaging system having an x-ray source and a digital x-ray detector, wherein the detector comprises rows and columns of pixels, the method comprising:

moving the x-ray source in a selected direction to a plurality of imaging positions while maintaining the detector stationary;

determining a binning direction that is parallel to the rows of pixels in the detector or to the columns of pixels in the detector based on a hardware configuration of the detector and that is parallel to the selected direction of moving the x-ray source;

acquiring the plurality of 2-D radiographic images of the subject each at one of the plurality of imaging positions, including combining captured image data in two or more pixels of the detector that are adjacent to each other in to the determined binning direction;

reconstructing the 3-D radiographic image of the subject using the acquired plurality of 2-D radiographic images; and displaying at least a portion of the reconstructed 3-D radiographic image.

2. The method of claim 1, further comprising connecting the rows of pixels to a gate driver configured to simultaneously activate two or more rows of the pixels.

3. The method of claim 2, further comprising reading out image data captured in any pixels in a column that are activated by the gate driver.

4. The method of claim 1, wherein the step of acquiring includes not combining image data captured in adjacent pixels of the detector that are not adjacent in the determined binning direction.

5. The method of claim 4, wherein the step of reconstructing the 3-D radiographic image includes using a same voxel resolution that is used for captured image data in the two or more adjacent pixels that are not combined.

6. The method of claim 1, wherein the step of combining captured image data includes determining an average pixel value of the two or more adjacent pixels and using the average pixel value as the pixel value in each of the two or more adjacent pixels.

7. A computer implemented method for tomographic image reconstruction using a radiographic imaging system having one or more x-ray sources and a digital detector, the method comprising:

acquiring a plurality of radiographic images of a subject in the digital detector, including acquiring the radiographic images each at one of a plurality of positions during a relative motion as between the one or more x-ray sources and the digital detector, wherein the relative motion is parallel to a row orientation of pixels in the detector or to a column orientation of the pixels in the detector; and reading out the radiographic images of the subject from the detector, including combining captured image data in two or more pixels of the detector that are adjacent to each other in a direction parallel to the row orientation of pixels in the detector or parallel to the column orientation of the pixels in the detector, including selecting the direction parallel to the row orientation or the column orientation and parallel to the relative motion direction of the detector and based on a hardware configuration of the detector.

8. The method of claim 7, further comprising connecting the pixels in the row orientation to a gate driver configured to simultaneously activate two or more rows of the pixels in the row orientation.

9. The method of claim 8, further comprising reading out image data captured in any pixels in the column orientation that are activated by the gate driver.

10. The method of claim 7, wherein the step of combining captured image data includes determining an average pixel value of the two or more pixels of the detector that are adjacent to each other and using the average pixel value to represent the combined captured image data in the two or more adjacent pixels.

11. A computer implemented method for tomographic image reconstruction using a radiographic imaging system having one or more x-ray sources and a digital detector, the method comprising:

determining a binning direction to be used to acquire radiographic images of a subject consistent with a direction of a relative motion as between the one or more x-ray sources and the subject, and determining the binning direction based on a hardware configuration of the digital detector;

capturing a plurality of projection images of the subject in the detector including changing the relative angle as between the one or more x-ray sources and the subject for each captured projection image;

binning the image data of each projection image captured in the detector in the determined binning direction to acquire the radiographic images of the subject;

reconstructing a tomographic image of the subject using the acquired radiographic images of the subject; and displaying at least a portion of the reconstructed tomographic image.

12. The method of claim 11, wherein the step of determining a binning direction comprises generating orientation instructions and displaying the orientation instructions to an operator.

13. The method of claim 12, wherein the step of generating orientation instructions comprises providing one or more signals to an actuator to rotate the detector.

14. The method of claim 11, further comprising connecting rows of pixels in the detector to a gate driver configured to simultaneously activate two or more rows of the pixels.

15. The method of claim 14, further comprising reading out image data captured in any pixels in a column that are activated by the gate driver.

16. The method of claim 11, wherein the step of determining the binning direction comprises determining an anatomical portion of a subject being imaged.

17. The method of claim 16, wherein the step of determining the binning direction further comprises looking up the binning direction in a LUT using the anatomical portion as an index into the LUT.

18. The method of claim 11, wherein the step of capturing a plurality of projection images comprises individually energizing x-ray sources in an array of carbon nanotube x-ray sources.

\* \* \* \* \*